United States Patent [19]

Kornreich et al.

[11] Patent Number: 5,235,036
[45] Date of Patent: Aug. 10, 1993

[54] CRF ANALOGS

[75] Inventors: Wayne D. Kornreich, San Diego, Calif.; Jean-Francois Hernandez, Oullins, France; Jean E. F. Rivier; Wylie W. Vale, Jr., both of La Jolla, Calif.

[73] Assignee: The Salk Institute for Biological Studies, San Diego, Calif.

[21] Appl. No.: 709,091

[22] Filed: May 31, 1991

[51] Int. Cl.$^5$ .............................. C07K 7/38; C07K 7/10
[52] U.S. Cl. .................................. 530/306; 530/324; 530/325; 930/21; 930/70; 930/260
[58] Field of Search ............... 514/9, 2, 805; 530/306, 530/324, 325; 930/21, 70, 260

[56] References Cited

U.S. PATENT DOCUMENTS

| | | | |
|---|---|---|---|
| 3,761,459 | 9/1973 | Pless | 530/324 |
| 3,770,715 | 11/1973 | Tesser et al. | 530/324 |
| 3,792,033 | 2/1974 | Iselin et al. | 530/306 |
| 4,415,546 | 11/1983 | Ramachandran et al. | 530/306 |
| 4,415,558 | 11/1983 | Vale et al. | 514/12 |
| 4,489,163 | 12/1984 | Rivier et al. | 436/86 |
| 4,594,329 | 6/1986 | Vale et al. | 514/12 |

OTHER PUBLICATIONS

Rivier et al, Proc. Nat'l Acad. Sci. USA. vol. 80, pp. 4851-4855, (Aug. 1983).
Rivier et al, Science, vol. 224, pp. 889-891, (May 22, 1984).
Shibahara et al, The EMBO Journal, vol. 2(5), pp. 775-779, (1983).
Rihel, Proceedings of the Biochemical Society, 56 p., vol. 125, (1971).
Hulliger et al, Acta Endocrinologica, vol. 75, pp. 24-32, (F174).

Primary Examiner—Merrell C. Cashion, Jr.
Assistant Examiner—T. D. Wessendorf
Attorney, Agent, or Firm—Fitch, Even, Tabin & Flannery

[57] ABSTRACT

Analogs of CRF, which are based upon hCRF, oCRF and alpha-helical CRF, are disclosed that can be administered to achieve a substantial elevation of ACTH, β-endorphin, β-lipotropin, other products of the pro-opiomelanocortin gene and corticosterone levels. Analogs include those having the formula: Y-$R_1$-$R_2$-$R_3$-$R_4$-$R_5$-Ile-Ser-Leu-Asp-Leu-Thr-Phe-His-Leu-Leu-Arg-Glu-Val-Leu-$R_{20}$-$R_{21}$-$R_{22}$-$R_{23}$-$R_{24}$-$R_{25}$-Gln-Leu-Ala-Gln-Gln-Ala-$R_{32}$-Ser-Asn-Arg-Lys-Leu-$R_{38}$-$R_{39}$-Ile-$R_{41}$-$NH_2$, wherein Y is an acyl group having 7 or fewer carbon atoms or hydrogen; $R_1$ is Ser or des$R_1$; $R_2$ is Glu, Gln or des$R_2$; $R_3$ is Glu or des$R_3$; $R_4$ is Pro or des$R_4$; $R_5$ is Pro or des$R_5$; $R_{20}$ is Ala or Glu; $R_{21}$ is Met or Nle; $R_{22}$ is Ala or Thr; $R_{23}$ is Arg or Lys; $R_{24}$ is D-Ala or Ala; $R_{25}$ is Glu or Asp; $R_{32}$ is D-His or His; $R_{38}$ is Met, Nle or Leu; $R_{39}$ is Ala, Glu or Asp; $R_{41}$ is Ile or Ala; provided however that at least one of $R_{20}$ and $R_{39}$ is Ala. One example is [Ala$^{20}$]-oCRF. These analogs or their pharmaceutically acceptable salts, dispersed in an acceptable liquid or solid carrier, can be administered to humans.

6 Claims, No Drawings

CRF ANALOGS

This invention was made with Government support under grant numbers HD-13527 and DK 26741 awarded by the National Institutes of Health. The Government has certain rights in this invention.

This invention is directed to peptides and to methods for pharmaceutical treatment of mammals using such peptides. More specifically, the invention relates to analogs of the hentetracontapeptide CRF, to pharmaceutical compositions containing such CRF analogs and to methods of treatment of mammals using such CRF analogs.

BACKGROUND OF THE INVENTION

Experimental and clinical observations have supported the concept that the hypothalamus plays a key role in the regulation of adenohypophysial corticotropic cells secretory functions. Although over 25 years ago, it was demonstrated that factors present in the hypothalamus would increase the rate of ACTH secretion by the pituitary gland, when incubated in vitro or maintained in an organ culture, a physiologic corticotropin releasing factor (CRF) was not characterized until ovine CRF (oCRF) was characterized in 1981. As disclosed in U.S. Pat. No. 4,415,558, oCRF was found to have the formula (SEQ ID NO:1): Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg Lys-Leu-Leu-Asp-Ile-Ala wherein the C-terminus is amidated. oCRF lowers blood pressure in mammals and stimulates the secretion of ACTH and β-endorphin.

Rat CRF(rCRF) was later isolated, purified and characterized as a hentetracontapeptide having the formula (SEQ ID NO:2): Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg -Lys-Leu-Met-Glu-Ile-Ile, wherein the C-terminus is amidated, as described in U.S. Pat. No. 4,489,163. It is sometimes referred to as rat amunine. The formula of human CRF has now been determined to be the same as that of rCRF, and the terms rCRF and hCRF are used interchangeably. A CRF analog having a high alpha-helical forming potential and the formula (SEQ ID NO:3): Ser-Gln-Glu-Pro-Pro-Ile-Ser-Leu-Asp-Leu-Thr-Phe--His- -Leu-Leu-Arg-Glu-Met-Leu-Glu-Met-Ala-Lys-Ala-Glu-Gln-Glu-Ala-Glu-Gln-Ala-Ala-Leu-Asn-Arg -Leu-Leu-Leu-Glu-Glu-Ala, wherein the C-terminus is amidated, has been developed; it is referred to as AHC (alphahelical CRF) and is described in U.S. Pat. No. 4,594,329.

Synthetic rCRF, oCRF and AHC stimulate ACTH and β-endorphin-like activities (β-END-LI) in vitro and in vivo and substantially lower blood pressure.

SUMMARY OF THE INVENTION

Analogs of these 41-residue CRF peptides have been discovered which exhibit greater biological activity in vitro than the native, peptides. These peptides have at least one Ala substitution in the 20-or the 39-position, and the peptides may optionally also have D-Phe in the 12-position, D-Ala in the 24-position and/or D-His in the 32-position, and Norleucine may be substituted in the 18, 21 and/or 38 positions. The Leu residue in the 37-position can be substituted with a methyl group on its α-carbon atom, as can be other Leu residues as well as the Ala residues, and such are considered to be equivalents for purposes of this application. Beginning at the N-terminus, the peptide can be optionally shortened by the deletion of 1 to about 5 residues, and is preferably shortened by deletion of about 4 residues. The N-terminus of the peptide is optionally acylated.

Pharmaceutical compositions in accordance with the invention include such CRF analogs, or nontoxic addition salts thereof, dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, β-endorphin, β-lipotropin, other products of the pro-opiomelanocortin gene and corticosterone and/or for the lowering of blood pressure and/or for affecting mood, behavioral and gastrointestinal functions and autonomic nervous system activities. Furthermore CRF analogs may be used for the evaluation of the status of pituitary, cardiovascular, gastrointestinal or central nervous system functions.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn= L-ornithine, Nle=L-norleucine, Nva=L-norvaline and Har=L-homoarginine. In addition the following abbreviations are used: CML=C$^\alpha$CH$_3$-L-leucine; Aib=C$^\alpha$CH$_3$-L-alanine or 2-aminoisobutyric acid.

The invention provides analogs of CRF having the following Formula (I): Y-$R_1$-$R_2$-$R_3$-$R_4$-$R_5$-Ile-Ser-Leu-Asp-Leu-Thr-Phe-His-Leu-Leu-Arg-Glu-Val-Leu -$R_{20}$-$R_{21}$-$R_{22}$-$R_{23}$-$R_{24}$-$R_{25}$-Gln-Leu-Ala-Gln-Gln-Ala-$R_{32}$-Ser-Asn-Arg-Lys-Leu-$R_{38}$-$R_{39}$-Ile-$R_{41}$-NH$_2$, wherein Y is an acyl group having 7 or fewer carbon atoms or hydrogen; $R_1$ is Ser or des$R_1$; $R_2$ is Glu, Gln or des$R_2$; $R_3$ is Glu or des$R_3$; $R_4$ is Pro or des$R_4$; $R_5$ is Pro or des$R_5$; $R_{20}$ is Ala or Glu; $R_{21}$ is Met or Nle; $R_{22}$ is Ala or Thr; $R_{23}$ is Arg or Lys; $R_{24}$ is D-Ala or Ala; $R_{25}$ is Glu or Asp; $R_{32}$ is D-His or His; $R_{38}$ is Met, Nle or Leu; $R_{39}$ is Ala, Glu or Asp; $R_{41}$ is Ile or Ala; provided however that at least one of $R_{20}$ and $R_{39}$ is Ala. Nontoxic addition salts of these peptides can be used as well. These analogs remain potent even if slightly shortened at the N-terminus, i.e., by a sequence of up to about 6 residues.

In a broader sense, the invention provides analogs of CRF of the following Formula (II): Y-$R_1$-$R_2$-$R_3$-$R_4$-$R_5$-Ile-Ser-$R_8$-$R_9$-Leu-$R_{11}$-$R_{12}$-$R_{13}$-$R_{14}$-Leu-Arg -$R_{17}$$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-Gln-Ala-$R_{32}$-$R_{33}$-Asn-Arg-$R_{36}$-$R_{37}$-$R_{38}$-$R_{39}$-$R_{40}$-$R_{41}$-NH$_2$ wherein Y is an acyl group having 7 or fewer carbon atoms or hydrogen; $R_1$ is Ser, D-Ser or des$R_1$; $R_2$ is Glu, Gln, pGlu, D-pGlu or des$R_2$; $R_3$ is Glu, Gly, D-Tyr or des$R_3$; $R_4$ is Pro, D-Pro or des$R_4$; $R_5$ is Pro or des$R_5$; $R_8$ and $R_{19}$ are selected from the group consisting of Leu, Ile, Ala, Gly, Val, Nle, Phe and Gln; $R_9$ is Asp or Glu; $R_{11}$ is Thr or Ser; $R_{12}$ is Phe, D-Phe, Leu, Ala, Ile, Gly, Val, Nle or Gln; $R_{13}$ is His, Tyr or Glu; $R_{14}$ is Leu or Met; $R_{17}$ is Glu or Lys; $R_{18}$ is Val, Nle or Met; $R_{20}$ is Ala or Glu; $R_{21}$ is Arg, Met, Nva, Ile, Ala, Leu, Nle, Val, Phe or Gln; $R_{22}$ is Ala, Thr, Asp or Glu; $R_{23}$ is Arg, Orn, Har or Lys; $R_{24}$ is Ala, D-Ala, Met, Leu, Ile, Gly, Val, Nle, Phe and Gln; $R_{25}$ is Glu, Ala or Asp; $R_{26}$ is Gly, Gln, Asn or Lys; $R_{27}$ is Leu, Ile, Ala, Val, Nva, Met, Nle, Phe, Asp, Asn, Gln or Glu; $R_{28}$ is Ala, Arg or Lys; $R_{29}$ is Gln, Ala or Glu; $R_{32}$ is Leu, His, D-His, Gly, Tyr or Ala; $R_{33}$ is Ile, Ser, Asn, Leu, Thr or Ala; $R_{36}$ is Asn, Lys, Orn, Arg, Har or Leu; $R_{37}$ is Leu or Tyr; $R_{38}$ is Met, Nle or Leu; $R_{39}$ is Ala, Glu or Asp; $R_{40}$ is Ile, Thr, Glu, Ala, Val, Leu, Nle, Phe, Nva, Gly, Asn or Gln; $R_{41}$ is Ile, Ala, Gly, Val, Leu, Nle, Phe or Gln, provided however that at least one of $R_{20}$ or $R_{39}$ is Ala, as well as nontoxic salts thereof.

A subgroup of these analogs which particularly include residues having a high alpha-helical forming potential are those having the following Formula (III): Y-$R_1$-$R_2$-$R_3$-$R_4$-$R_5$-Ile-Ser-Leu-$R_9$-Leu-Thr-$R_{12}$-$R_{13}$-$R_{14}$-Leu-Arg-Glu-$R_{18}$-Leu -$R_{20}$-$R_{21}$-Ala-Lys-$R_{24}$-Glu-Gln-$R_{27}$-Ala-Glu-Gln-Ala-$R_{32}$-$R_{33}$-Asn-Arg-$R_{36}$-$R_{37}$-$R_{38}$-$R_{39}$-$R_{40}$-$R_{41}$-$NH_2$ wherein Y is an acyl group having 7 or fewer carbon atoms or hydrogen; $R_1$ is Ser or des$R_1$; $R_2$ is Glu, Gln or des$R_2$; $R_3$ is Glu or des$R_3$; $R_4$ is Pro or des$R_4$; $R_5$ is Pro or des$R_5$; $R_9$ is Asp or Glu; $R_{12}$ is Phe, D-Phe or Leu; $R_{13}$ is His or Glu; $R_{14}$ is Leu or Met; $R_{18}$ is Nle or Met; $R_{20}$ is Ala or Glu; $R_{21}$ is Met, Nle or Ile; $R_{24}$ is Ala or D-Ala; $R_{27}$ is Glu or Leu; $R_{32}$ is His, D-His or Ala; $R_{33}$ is Ser or Leu; $R_{36}$ is Leu or Lys; $R_{37}$ is Leu or Tyr; $R_{38}$ is Leu or Nle; $R_{39}$ is Ala, Glu or Asp; $R_{40}$ is Ile or Glu and $R_{41}$ is Ile, Ala or Val; provided however that at least one of $R_{20}$ and $R_{39}$ is Ala.

The peptides are synthesized by a suitable method, such as by exclusively solid-phase techniques, by partial solid-phase techniques, by fragment condensation or by classical solution addition. Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Thus, chemical synthesis of such a peptide analog may result in the formation of an intermediate of the Formula (IA): $X^1$-$R_1(X^2)$-$R_2(X^4$ or $X^5)$-$R_3(X^5)$-$R_4$-$R_5$-Ile-Ser $(X^2)$-Leu-Asp$(X^5)$-Leu-Thr$(X^2)$-$R_{12}$-His$(X^7)$-Leu-Leu-Arg$(X^3)$-Glu$(X^5)$-Val-Leu-$R_{20}(X^5)$ -$R_{21}$-$R_{22}(X^2)$-$R_{23}(X^3$ or $X^6)$-$R_{24}$-$R_{25}(X^5)$-Gln$(X^4)$-Leu-Ala-Gln$(X^4)$-Gln $(X^4)$-Ala-$R_{32}(X^7)$-Ser$(X^2)$-Asn$(X^4)$-Arg$(X^3)$-Lys$(X^6)$-Leu-$R_{38}$-$R_{39}(X^5)$-Ile -$R_{41}$-$X^8$ wherein: the R-groups are as hereinbefore defined.

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl, acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenylmethyloxycarbonyl (FMOC), cyclopentyloxycarbonyl, adamantyloxycarbonyl, and cyclohexyloxycarbonyl; and (5) thiourethan-type protecting groups, such as phenylthiocarbonyl. The preferred alpha-amino protecting group is BOC if the synthesis employs acid-catalyzed removal of the alpha-amino protecting groups; however, for syntheses employing a base-catalyzed removal strategy, FMOC is preferred, in which case more acid-labile side-chain protecting groups can be used, including t-Butyl esters or ethers as well as BOC.

$X^2$ is a protecting group for the hydroxyl group of Thr and Ser and is generally selected from the class containing acetyl(Ac), benzoyl(Bz), tert-butyl(t-Bu), triphenylmethyl(trityl), tetrahydropyranyl, benzyl ether(Bzl) and 2,6-dichlorobenzyl(DCB) when a BOC strategy is employed. The preferred protecting group is Bzl for a BOC strategy and t-Bu for FMOC strategy. $X^2$ can also be hydrogen, which means there is no protecting group on the hydroxyl group.

$X^3$ is a protecting group for the guanidino group of Arg generally selected from the class containing nitro, p-toluenesulfonyl(Tos), Z, adamantyloxycarbonyl and BOC, or is hydrogen. Tos is preferred for a BOC strategy and 4-methoxy-2,3,6-trimethyl benzene sulfonyl (MTR) or pentamethylchroman-6-sulfonyl (PMC) for FMOC strategy.

$X^4$ is hydrogen or a suitable protecting group, preferably xanthyl(Xan), for the side chain amido group of Asn or Gln. Asn or Gln is preferably coupled without side chain protection in the presence of hydroxybenzotriazole (HOBt).

$X^5$ is hydrogen or an ester-forming protecting group for the $\beta$- or $\gamma$-carboxyl group of Asp or Glu, and is generally selected from the class containing the esters of cyclohexyl(OChx), benzyl(OBzl), 2,6-dichlorobenzyl, methyl, ethyl and t-butyl(Ot-Bu). OChx is preferred for a BOC strategy and Ot-Bu for FMOC strategy.

$X^6$ is hydrogen or a protecting group for the side chain amino substituent of Lys. Illustrative of suitable side chain amino protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore. 2-Cl-Z is preferred for a BOC strategy and BOC for FMOC strategy.

$X^7$ is hydrogen or a protecting group for the imidazole nitrogen of His such as Tos or 2,4-dinitrophenyl(DNP).

When Met is present, the sulfur may be protected, if desired, with oxygen.

The selection of a side chain amino protecting group is not critical except that it should must be one which is not removed during deprotection of the alpha-amino groups during the synthesis. Hence, the alpha-amino protecting group and the side chain amino protecting group cannot be the same.

$X^8$ is $NH_2$, a protecting group such as an ester or an anchoring bond used in solid phase synthesis for linking to a solid resin support, preferably one represented by the formulae:

—NH—benzhydrylamine (BHA) resin support and —NH—paramethylbenzhydrylamine (MBHA) resin support. Cleavage from a BHA or MBHA resin directly gives the CRF analog amide. By employing an N-methyl-derivative of such a resin, a methyl-substituted amide can be created.

In the formula for the intermediate, at least one of $X^1$, $X^2$, $X^3$, $X^4$, $X^5$, $X^6$ and $X^7$ is a protecting group. The particular amino acid chosen for each the R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the acyl group at the N-terminal represented by Y, acetyl, formyl, acrylyl and benzoyl are preferred. Moreover, as indicated hereinbefore, the N-terminus can be slightly shortened without significantly affecting biological potency.

Thus, there is also disclosed herein processes for the manufacture of compounds defined by the Formula (I) comprising (a) forming a peptide intermediate having at least one protective group and having the Formula (IA) wherein: $X^1$, $X^2$, $X^3$, $X^4$, $X^5$, $X^6$ and $X^7$ are each either hydrogen or a protective group, and $X^8$ is either a protective group or an anchoring bond to resin support or $NH_2$ and (b) splitting off the protective group or groups or anchoring bond from said peptide intermediate of the Formula (IA) and (c) if desired, converting a resulting peptide into a nontoxic addition salt thereof.

When the peptides are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for rCRF analogs can be prepared by attaching alpha-amino-protected Ile to a BHA or MBHA resin.

Ile protected by BOC is coupled to the BHA or MBHA resin using methylene chloride and dimethylformamide (DMF). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used as described in Schroder & Lubke, "The Peptides", Vol. 1, pp. 72–75 (Academic Press 1965).

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCC) and N,N'-diisopropyl carbodiimide(DICI).

The activating reagents used in the solid phase synthesis of the peptides are well known in the peptide art. Examples of suitable activating reagents are carbodiimides, such as DCC, DICI and N-ethyl-N'-(3-dimethylaminopropyl) carbodiimide. Other activating reagents and their use in peptide coupling are described by Schroder & Lubke, supra, in Chapter III, and by Kapoor, *J. Phar. Sci.*, 59, pp 127 (1970). P-nitrophenyl ester (ONp) may also be used to activate the carboxyl end of Asn or Gln for coupling. For example, BOC-Asn(ONp) can be coupled overnight using one equivalent of HOBt in a 50% mixture of DMF and methylene chloride, in which case no DCC is added.

Each protected amino acid or amino acid sequence is introduced into the solid phase reactor in about a four-fold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.*, 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., *Biopolymers*, 17, pp. 1927–1938, (1978).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X_3$, $X^4$, $X^5$, $X^6$ and $X^7$ and the alpha-amino protecting group $X^1$ (unless it is an acyl group which is intended to be present in the final peptide) to obtain the peptide. When using hydrogen fluoride for cleaving, anisole or cresole and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate potential S-alkylation.

The following Example sets forth the preferred method for synthesizing CRF analogs by the solid-phase technique.

EXAMPLE I

The synthesis of [$Ala^{20}$]-oCRF having the formula (SEQ ID NO:4): Ser-Gln-Glu-Pro-Pro-Ile-Ser-Leu-Asp-Leu-Thr-Phe-His-Leu-Leu-Arg-Glu-Val-Leu-Ala- Met-Thr-Lys-Ala-Asp-Gln-Leu-Ala-Gln-Gln-Ala-His-Ser-Asn-Arg-Lys -Leu-Leu-Asp-Ile-Ala is, wherein the C-terminus is amidated, conducted in a stepwise manner on a MBHA hydrochloride resin, such as available from Bachem, Inc., having a substitution range of about 0.1 to 0.5 mmoles/gm. resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | $CH_2Cl_2$ wash-80 ml. (2 times) | 3 |
| 2 | Methanol (MeOH) wash-30 ml. (2 times) | 3 |
| 3 | $CH_2Cl_2$ wash-80 ml. (3 times) | 3 |
| 4 | 50 percent TFA plus 5 percent 1,2-ethane-dithiol in $CH_2Cl_2$-70 ml. (2 times) | 12 |
| 5 | Isopropanol wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30-300 |

Coupling of BOC-Ile results in the substitution of about 0.35 mmol. Ile per gram of resin. All solvents that are used are carefully degassed, preferably by sparging with an inert gas, e.g., helium or nitrogen, to insure the absence of oxygen that might undesirably oxidize the sulfur of the Met residue.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser and Thr. BOC-Asn or BOC-Gln is coupled in the presence of using one equivalent of DCC and two equivalents of HOBt in a 50% mixture of DMF and methylene chloride. 2-Cl-Z is used as the protecting group for the Lys side chain. Tos is used to protect the guanidino group of Arg and the imidazole group of His, and the side-chain carboxyl group of Glu or Asp is protected by OChx. At the end of the synthesis, the following composition is obtained: BOC-Ser(Bzl)-Gln-Glu(OChx)-Pro-Pro-Ile-Ser(Bzl)-Leu-Asp(OChx)-Leu-Thr(Bzl)-Phe-His(Tos)-Leu-Leu-Arg(Tos)-Glu(OChx)-Val-Leu-Ala-Met-Thr(Bzl)-Lys (2-Cl-Z)-Ala-Asp(OChx)-Gln-Leu-Ala-Gln-Gln-Ala-His(Tos)-Ser(Bzl)-Asn-Arg(Tos)-Lys(2-Cl-Z)-Leu-Leu-Asp(OChx)-Ile-Ala-resin support.

In order to cleave and deprotect the resulting protected peptide-resin, it is treated with 1.5 ml. anisole, 0.5 ml. of methylethylsulfide or dimethylsulfide and 15 ml. hydrogen fluoride (HF) per gram of peptide-resin, first at $-20°$ C. for 20 min. and then at $0°$ C. for one and one-half hours. After elimination of the HF under high vacuum, the resin-peptide is washed with dry diethyl ether, and the peptide is then extracted with de-gassed 2N aqueous acetic acid or a 1:1 mixture of acetonitrile and water, separated from the resin by filtration, and lyophilized.

The lyophilized peptide is then purified by preparative or semi-preparative HPLC as described in Rivier, et al., J. Chromatography, 288, 303-328 (1984); and Hoe-ger, et al., BioChromatography, 2,3, 134-142 (1987). The chromatographic fractions are carefully monitored by HPLC, and only the fractions showing substantial purity are pooled.

The peptide is judged to be homogeneous by reversed-phase high performance liquid chromatography using a Waters HPLC system with a $0.46 \times 25$ cm. column packed with 5 $\mu$m $C_{18}$ silica, 300 Å pore size. The determination is run at room temperature using gradient conditions with 2 buffers. Buffer A is an aqueous trifluoroacetic acid (TFA) solution consisting of 1.0 ml. of TFA per 1000 ml. of solution. Buffer B is 1 ml TFA diluted to 400 ml with $H_2O$ which is added to 600 ml. of acetonitrile. The analytical HPLC was run under gradient condition of 55 vol. % Buffer B to 85 vol. % Buffer B over 30 minutes. At a flow rate of 2 ml. per minute, the retention time is 17.0 minutes. If 2.25 molar triethylammonium phosphate (TEAP) is used Buffer A and Buffer B consists of 60% acetonitrile in Buffer A, under gradient conditions of 50% Buffer B to 80% Buffer B over a 30-minute period, a retention time of 16.2 minutes is obtained.

Specific optical rotation of the CRF analog peptide, which is synthesized and purified in the foregoing manner, is measured on a Perkin Elmer Model 241 Polarimeter as $[\alpha]_D^{22} = -91.8° \pm 1.0$ (c=1 in 1% acetic acid) (without correction for the presence of $H_2O$ and TFA); it has a purity of greater than about 95%. Purity is further confirmed by mass spectroscopy (MS) and capillary zone electrophoresis.

To check whether the precise sequence is achieved, the CRF analog is hydrolyzed in sealed evacuated tubes containing 4 molar methane sulfonic acid, 3 $\mu$l of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 41-residue peptide structure has been obtained.

EXAMPLE II

The peptide [$Ala^{39}$]-oCRF having the formula (SEQ ID NO:5):
Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg -Lys-Leu-Leu-Ala-Ile-Ala wherein the C-terminus is amidated is synthesized using a procedure generally as set forth in Example I.

The peptide is judged to be homogeneous by reversed-phase high performance liquid chromatography using a Waters HPLC system with a $0.46 \times 25$ cm. column packed with 5 $\mu$m $C_{18}$ a silica, 300 Å pore size. The determination is run at the same conditions as in Example I with the retention time for the TFA buffer system being 16.6 minutes. When the triethylammonium phosphate (TEAP) buffer system is used, the retention time is 17.4 minutes.

Specific optical rotation of the CRF peptide, which is synthesized and purified in the foregoing manner, is measured on a Perkin Elmer Model 241 Polarimeter as $[\alpha]_D^{22} = -81.1° \pm 1.0$ (c=0.5 in 1% acetic acid) (without correction for the presence of $H_2O$ and TFA); it has a purity of greater than about 90%.

Amino acid analysis of the resultant, purified peptide is consistent with the formula for the prepared peptide and confirms that the 41-residue peptide structure is obtained.

The synthetic peptides [Ala$^{20}$]-oCRF and [Ala$^{39}$]-oCRF are examined for their effects on the secretion of ACTH and β-endorphin in vitro and also in vivo. The potency of synthetic oCRF analogs to stimulate the secretion of ACTH and β-endorphin by cultured rat pituitary cells is measured using the procedure as generally set forth in *Endocrinology*, 91, 562 (1972) and compared against synthetic oCRF. [Ala$^{20}$]-oCRF is considered to be about 2 to 4 times as potent as the native hormone. Similar tests of [Ala$^{39}$]-oCRF showed about an 85% increase in biopotency in vitro over the native hormone. In vivo testing which can be carried out using the general procedure set forth in C. Rivier et al., *Science*. 218, 377 (1982) shows biopotency to stimulate the secretion of ACTH and β-END-LI and a significant lowering of blood pressure when injected peripherally, e.g. intravenously.

EXAMPLE III

The peptide [Ala$^{20,29}$]-oCRF having the formula (SEQ ID NO:6):

Ser-Gln-Glu-Pro-Pro-Ile-Ser-Leu-Asp-Leu-Thr-Phe-His-Leu-Leu-Arg-Glu-Val-Leu-Ala-Met-Thr-Lys-Ala-Asp-Gln-Leu-Ala-Gln-Gln-Ala-His-Ser-Asn-Arg-Lys-Leu-Leu-Ala-Ile-Ala is synthesized using a procedure generally as set forth in Example I.

The peptide is purified and judged to be homogeneous using MS. Amino acid analysis of the resultant, purified peptide is consistent with the formula for the prepared peptide. The 41-residue peptide is biopotent and lowers blood pressure when injected peripherally.

EXAMPLE IV

The peptide [D-Phe$^{12}$, Ala$^{20}$]-rCRF(3-41) having the formula:

H-Glu-Pro-Pro-Ile-Ser-Leu-Asp-Leu-Thr-D-Phe-His-Leu-Leu-Arg-Glu-Val-Leu-Ala-Met-Ala-Arg-Ala-Glu-Gln-Leu-Ala-Gln-Gln-Ala-His-Ser-Asn-Arg-Lys-Leu-Met-Glu-Ile-Ile-NH$_2$ is synthesized. The peptide is likewise biopotent and causes significant lowering of blood pressure when injected peripherally.

EXAMPLE V

The peptide [Ala$^{20}$]-rCRF having the formula (SEQ ID NO:7):

Ser-Glu-Glu-Pro-Pro-Ile-Ser-Leu-Asp-Leu-Thr-Phe-His-Leu-Leu-Arg-Glu-Val-Leu-Ala-Met-Ala-Arg-Ala-Glu-Gln-Leu-Ala-Gln-Gln-Ala-His-Ser-Asn-Arg-Lys-Leu-Met-Glu-Ile-Ile wherein the C-terminus is amidated is synthesized using a procedure generally as set forth in Example I. The peptide is likewise biopotent and stimulates the secretion of ACTH and β-END-LI and causes significant lowering of blood pressure when injected peripherally.

EXAMPLE VI

The peptide [Ala$^{39}$-rCRF having the formula (SEQ ID NO:8):

Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg -Lys-Leu-Met-Ala-Ile-Ile wherein the C-terminus is amidated is synthesized using a procedure generally as set forth in Example I. The peptide is likewise biopotent, stimulates the secretion of ACTH and β-END-LI and causes significant lowering of blood pressure when injected peripherally.

EXAMPLE VII

Using the procedure set forth in Example I, the following peptides are also prepared:
[Acetyl-Ser$^1$, D-Phe$^{12}$, Ala$^{20}$, Nle$^{21,38}$]-rCRF
[D-Phe$^{12}$, Ala$^{20,22}$]-oCRF
[D-Phe$^{12}$, Ala$^{20,32}$, D-Ala$^{24}$]-rCRF(4-41)
[D-Phe$^{12}$, Nle$^{21}$, Ala$^{39}$]-oCRF
[Formyl-Ser$^1$, D-Phe$^{12}$, Ala$^{20}$, Nle$^{21,38}$, D-His$^{32}$]-rCRF
[Ala$^{20,25}$, D-Ala$^{24}$]-oCRF
[D-Phe$^{12}$, Ala$^{20}$, D-Ala$^{24}$]-rCRF(2-41)
[Ala$^{20}$, D-Ala$^{24}$, Nle$^{21,38}$, Ala$^{39}$]-oCRF
[Benzoyl-Ser$^7$, D-Phe$^{12}$, Ala$^{20}$, Nle$^{21,38}$, D-His$^{32}$]-rCRF
[D-His$^{32}$, Ala$^{39}$]-oCRF
[D-Phe$^{12}$, Ala$^{20,33}$, D-Ala$^{24}$, D-His$^{32}$]-rCRF(6-41)
[Ala$^{20,29}$, Nle$^{21}$, D-His$^{32}$]-oCRF
[Acrylyl-Glu$^2$, Ala$^{20}$, Nle$^{21,38}$, D-His$^{32}$]-rCRF(2-41)
[Nle$^{18,21}$, Ala$^{20,29}$, D-His$^{32}$]-AHC
[D Pro$^4$, D-Phe$^{12}$, Nle$^{18,21}$, Ala$^{20,32}$, Ile$^{33}$, Asn$^{36}$]-AHC
[D-Tyr$^3$, Nle$^{18}$, Nva$^{21}$, Ala$^{20,33}$, D-Ala$^{24}$]-AHC
[Glu$^{2,13,22}$, D-Phe$^{12}$, Nle$^{18}$, Orn$^{23}$, Ala$^{39}$]-AHC
[D-Phe$^{12}$, Glu$^{13}$, Ala$^{20}$, Ile$^{21}$, Lys$^{36}$, Tyr$^{37}$, Val$^{41}$]-AHC
[D-Phe$^{12}$, Ala$^{20,39,40}$, Arg$^{21}$]-AHC
[Nle$^{18,21}$, Ala$^{20,39}$]-AHC
[Ala$^{20}$]-AHC
[Ala$^{39}$]-AHC
[Ala$^{20,39}$, Nle$^{21}$, CML$^{37}$]-oCRF
[D-Phe$^{12}$, Ala$^{20,32}$, Nle$^{21,38}$, CML$^{37}$]-oCRF
[Ala$^{20}$, Nle$^{21,38}$, D-His$^{32}$, CML$^{37}$]-oCRF These peptides are biopotent in stimulating the secretion of ACTH and β-END-LI.

EXAMPLE VIII

Using the procedure set forth in Example I, the following peptides are also prepared which are CRF antagonists:
[Ala$^{20}$]-AHC(9-41)
[Ala$^{39}$]-AHC(12-41)
[Ala$^{20}$]-oCRF(10-41)
[D-Phe$^{12}$, Ala$^{20}$, Nle$^{21,38}$]-rCRF(12-41)
[D-Phe$^{12}$, Ala$^{20}$]-oCRF(12-41)
[Nle$^{18,21}$, Ala$^{20,39}$]-AHC(10-41)
[D-Phe$^{12}$, Ala$^{20}$]-rCRF(12-41)
[D-Phe$^{12}$, Nle$^{21}$, Ala$^{39}$]-oCRF(12-41)
[D-Phe$^{12}$, Ala$^{20,39}$]-AHC(12-41)
[D-Phe$^{12}$, Ala$^{20}$, Nle$^{21,38}$]-rCRF(12-41)
[Ala$^{20}$, D-Ala$^{24}$]-oCRF(11-41)
[Nle$^{18,21}$, Ala$^{20}$, D-His$^{32}$]-AHC(11-41)
[D-Phe$^{12}$, Ala$^{20}$, D-Ala$^{24}$]-rCRF(12-41)
[Ala$^{20}$, Nle$^{21,38}$, D-His$^{32}$]-rCRF(10-41)
[D-His$^{32}$, Ala$^{39}$]-oCRF(9-41)
[D-Phe$^{12}$, Ala$^{20}$, D-His$^{32}$]-rCRF(12-41)
[Ala$^{20}$, Nle$^{21,38}$, Ala$^{39}$]-oCRF(9-41)
[Ala$^{20}$, Nle$^{21}$]-oCRF(10-41)
[Ala$^{20}$, Nle$^{21,38}$, D-His$^{32}$]-rCRF(9-41)
[Nle$^{18}$, Ala$^{20}$, D-Ala$^{24}$]-AHC(10-41)
[D-Phe$^{12}$, Nle$^{18}$, Ala$^{39}$]-AHC(12-41)
[D-Phe$^{12}$, Nle$^{18,21}$, Ala$^{20}$]-AHC(12-41)
[D-Phe$^{12}$, Ala$^{20}$, Lys36]-AHC(12-41)
[Ala$^{20}$, Nle$^{21}$, D-His$^{32}$, CML$^{37}$]-oCRF(11-41)
[Ala$^{20}$, Nle$^{21,38}$ CML$^{37}$]-oCRF(10-41)
[D-Phe$^{12}$, Ala$^{20}$, Nle$^{21,38}$, CML$^{37}$]-oCRF(12-41)

These CRF antagonist peptides are all considered to inhibit the secretion of ACTH and β-END-LI in response to various stimuli.

CRF profoundly stimulates the pituitary-adrenalcortical axis, and CRF agonists should be useful to stimulate the functions of this axis in some types of patients with low endogenous glucocorticoid production. For example, CRF should be useful in restoring pituitary-adrenal function in patients having received exogenous glucocorticoid therapy whose pituitary- adrenalcortical functions remain supressed.

Most other regulatory peptides have been found to have effects upon the central nervous system and upon the gastrointestinal tract. Because ACTH and β-END secretion is the "sine qua non" of mammal's response to stress, it was not surprising that CRF has significant effects on the brain as a mediator of the body's stress response. For example, CRF in the brain appears to increase respiratory rate and may be useful in treating respiratory depression. CRF may also find application in modifying the mood, learning and behavior of normal and mentally disordered individuals. Because CRF analogs elevate the levels of ACTH, β-END, β-lipotropin, other pro-opiomelanocortin gene products and corticosterone, its administration can be used to induce their effects on the brain and periphery to thereby influence memory, mood, pain appreciation, etc., and more specifically, alertness, depression and/or anxiety. For example, when administered into the ventricles, CRF increases activity and improves learning performance in rats and thus may function as a natural stimulant.

CRF analogs should also be of use for increasing blood flow to the gastrointestinal tract of mammals, particularly humans and other mammals. All CRF related peptides have been shown to dialate the mesenteric vascular bed. Also, oCRF inhibits gastric acid production, and CRF analogs are expected to also be effective in the treatment of gastric ulcers by reducing gastric acid production and/or inhibiting gastrointestinal functions in a mammal.

CRF analogs or the nontoxic addition salts thereof, combined with a pharmaceutically or veterinarily acceptable carrier to form a pharmaceutical composition, may be administered to mammals, including humans, either intravenously, subcutaneously, intramuscularly, percutaneously, e.g. intranasally, intracerebrospinally or orally. The peptides should be at least about 90% pure and preferably should have a purity of at least about 98%; however, lower purities are effective and may well be used with mammals other than humans. This purity means that the intended peptide constitutes the stated weight percent of all like peptides and peptide fragments present. Administration to humans may be employed by a physician to lower blood pressure or to stimulate endogenous glucocorticoid production. The required dosage will vary with the particular condition being treated, with the severity of the condition and with the duration of desired treatment.

These peptides may also be used to evaluate hypothalamic pituitary adrenal function in mammals with suspected endocrine or central nervous system pathology by suitable administration followed by monitoring body functions. For example, administration may be used as a diagnostic tool to evaluate Cushing's disease and affective disorders, such as depressive illness.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 1 to about 200 micrograms of the peptide per kilogram of the body weight of the host animal. In some instances, treatment of subjects with these peptides can be carried out in lieu of the administration of ACTH or corticosteroids, in such instances a dosage as low as about 10 ng/Kg of body weight may be employed. As used herein, all temperatures are 20° C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. In the examples given, substitutions at positions in the CRF peptide chain as known in this art, or with commonly accepted comparable residues, other than at the specified position-20 and position-39, can be made without detracting from the potency of the analogs, and peptides having such substitutions are considered to be equivalents. It appears important that the amino acid sequence, or equivalents thereof, from about position-7 through the C-terminus be present in the synthetic peptide to assure biopotency, whereas the remainder of the molecule does not appear as critical. For instance, instead of the simple amide at the C-terminus, a lower alkyl-substituted amide, e.g. methylamide, ethylamide, etc, may be incorporated without adversely affecting biological potency, and such peptides are also considered as equivalents.

Various features of the invention are emphasized in the claims which follow.

---

What is claimed is:

1. An ovine CRF agonist peptide which stimulates secretion of ACTH and β-endorphin, or a nontoxic addition salt thereof, having a formula selected from the group consisting of SEQ ID NO: 4, SEQ ID NO:5 and SEQ ID NO: 6, wherein the C-terminus is amidated.

2. The peptide of claim 1 having the formula: SEQ ID NO: 5 wherein the C-terminus is amidated.

3. The peptide of claim 1 having the formula: SEQ ID NO: 6 wherein the C-terminus is amidated.

4. An ovine CRF agonist peptide which stimulates secretion of ACTH and β-endorphin having a SEQ ID NO: 4 wherein the C-terminus is amidated, or a nontoxic addition salt thereof.

5. An ovine CRF agonist peptide which stimulates secretion of ACTH and β-endorphin having the formula:

H-Ser-Gln-Glu-Pro-Pro-Ils-Ser-Leu-Asp-Leu-Thr-Phe-His-Leu-Leu-Arg-Glu-Val-Leu-$R_{20}$-$R_{21}$-Thr-Lys-Ala-Asp-Gln-Leu-Ala-Gln-Gln-Ala-His-Ser-Asn-Arg-Lys-Leu-Leu-$R_{39}$-Ile-Ala-$NH_2$, wherein $R_{20}$ is Ala or Glu; $R_{21}$ is Met or Nle; and $R_{39}$ is Ala or Asp; provided however that at least one of $R_{20}$ and $R_{39}$ is Ala; or a nontoxic addition salt thereof.

6. The peptide of claim 5 wherein $R_{20}$ is Ala.

* * * * *

UNITED STATES PATENT AND TRADEMARK OFFICE
CERTIFICATE OF CORRECTION

PATENT NO. : 5,235,036
DATED : August 10, 1993
INVENTOR(S) : Kornreich, et al.

It is certified that error appears in the above-indentified patent and that said Letters Patent is hereby corrected as shown below:

Column 1, line 63, after "native", delete the comma (,); Column 6, line 51, change "$X_3$" to -- $X^3$ --; Column 7, line 2, delete "is"; Column 7, line 3, after "amidated,", insert --is--; Column 9, line 20, change "[$Ala^{20,29}$]" to --[$Ala^{20,39}$]--; Column 9, line 58, after "[$Ala^{39}$", insert --]--; Column 12, line 32, delete "20"; Column 18, line 10, change "Ils" to --Ile--.

Signed and Sealed this

Eighth Day of March, 1994

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
 ( A ) LENGTH: 41 amino acids
 ( B ) TYPE: amino acid
 ( D ) TOPOLOGY: unknown ( i i ) MOLECULE TYPE: peptide ( x i ) SEQUENCE DESCRIPTION: SEQ ID NO:1:

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35              40

( 2 ) INFORMATION FOR SEQ ID NO:2:

( i ) SEQUENCE CHARACTERISTICS:
 ( A ) LENGTH: 41 amino acids
 ( B ) TYPE: amino acid
 ( D ) TOPOLOGY: unknown ( i i ) MOLECULE TYPE: peptide ( x i ) SEQUENCE DESCRIPTION: SEQ ID NO:2:

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35              40

( 2 ) INFORMATION FOR SEQ ID NO:3:

( i ) SEQUENCE CHARACTERISTICS:
 ( A ) LENGTH: 41 amino acids
 ( B ) TYPE: amino acid
 ( D ) TOPOLOGY: unknown ( i i ) MOLECULE TYPE: peptide ( x i ) SEQUENCE DESCRIPTION: SEQ ID NO:3:

Ser Gln Glu Pro Pro Ile Ser Leu Asp Leu Thr Phe His Leu Leu Arg
1               5                   10                  15

Glu Met Leu Glu Met Ala Lys Ala Glu Gln Glu Ala Glu Gln Ala Ala
            20                  25 -                30

Leu Asn Arg Leu Leu Leu Glu Glu Ala
        35              40

( 2 ) INFORMATION FOR SEQ ID NO:4:

( i ) SEQUENCE CHARACTERISTICS:
 ( A ) LENGTH: 41 amino acids
 ( B ) TYPE: amino acid
 ( D ) TOPOLOGY: unknown ( i i ) MOLECULE TYPE: peptide ( x i ) SEQUENCE DESCRIPTION: SEQ ID NO:4:

Ser Gln Glu Pro Pro Ile Ser Leu Asp Leu Thr Phe His Leu Leu Arg
1               5                   10                  15

Glu Val Leu Ala Met Thr Lys Ala Asp Gln Leu Ala Gln Gln Ala His
            20                  25                  30

Ser Asn Arg Lys Leu Leu Asp Ile Ala
        35              40

( 2 ) INFORMATION FOR SEQ ID NO:5:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:5:

```
Ser Gln Glu Pro Pro Ile Ser Leu Asp Leu Thr Phe His Leu Leu Arg
 1               5                  10                  15
Glu Val Leu Glu Met Thr Lys Ala Asp Gln Leu Ala Gln Gln Ala His
            20                  25                  30
Ser Asn Arg Lys Leu Leu Ala Ile Ala
            35                  40
```

( 2 ) INFORMATION FOR SEQ ID NO:6:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

```
Ser Gln Glu Pro Pro Ile Ser Leu Asp Leu Thr Phe His Leu Leu Arg
 1               5                  10                  15
Glu Val Leu Ala Met Thr Lys Ala Asp Gln Leu Ala Gln Gln Ala His
            20                  25                  30
Ser Asn Arg Lys Leu Leu Ala Ile Ala
            35                  40
```

( 2 ) INFORMATION FOR SEQ ID NO:7:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

```
Ser Glu Glu Pro Pro Ile Ser Leu Asp Leu Thr Phe His Leu Leu Arg
 1               5                  10                  15
Glu Val Leu Ala Met Ala Arg Ala Glu Gln Leu Ala Gln Gln Ala His
            20                  25                  30
Ser Asn Arg Lys Leu Met Glu Ile Ile
            35                  40
```

( 2 ) INFORMATION FOR SEQ ID NO:8:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
Ser Glu Glu Pro Pro Ile Ser Leu Asp Leu Thr Phe His Leu Leu Arg
 1               5                  10                  15
Glu Val Leu Glu Met Ala Arg Ala Glu Gln Leu Ala Gln Gln Ala His
            20                  25                  30
Ser Asn Arg Lys Leu Met Ala Ile Ile
```